US00PP13267P3

(12) United States Plant Patent
Miyachi

(10) Patent No.: US PP13,267 P3
(45) Date of Patent: Nov. 26, 2002

(54) ZOYSIAGRASS PLANT 'HIMENO'

(75) Inventor: Yoshifumi Miyachi, Hiroshima (JP)

(73) Assignee: Zoysian Japan Co., Ltd., Akashi (JP)

( * ) Notice: Subject to any disclaimer, the term of this patent is extended or adjusted under 35 U.S.C. 154(b) by 0 days.

(21) Appl. No.: 09/757,653

(22) Filed: Jan. 11, 2001

(65) Prior Publication Data

US 2002/0092083 P1 Jul. 11, 2002

(51) Int. Cl.[7] ..... A01H 5/00
(52) U.S. Cl. ..... Plt./390
(58) Field of Search ..... Plt./390

(56) References Cited

U.S. PATENT DOCUMENTS

| | | | |
|---|---|---|---|
| PP5,845 | P | 12/1986 | Youngner |
| PP9,135 | P | 5/1995 | Gibeault et al. |
| PP10,187 | P | 1/1998 | Yaneshita et al. |

*Primary Examiner*—Bruce R. Campell
*Assistant Examiner*—Annette H. Para
(74) *Attorney, Agent, or Firm*—Oliff & Berridge, PLC

(57) ABSTRACT

A new and distinct variety of Zoysiagrass plant possessing a bluish deep green color, slow vertical growth, and minimal headings.

4 Drawing Sheets

LATIN NAME OF THE GENUS AND SPECIES OF THE PLANT CLAIMED

The present invention relates to the genus *Zoysia japonica,* species 'Himeno'.

BACKGROUND OF THE INVENTION

Field of Invention

The present invention relates to a new and distinct asexually reproduced variety of perennial Zoysiagrass (*Zoysia japonica*).

SUMMARY OF THE INVENTION

This invention relates to a new and distinct variety of Zoysiagrass plant that was discovered by the inventor growing among other cultivated Zoysiagrass varieties in the inventor's lawngrass collection in Hiroshima, Japan. This new variety of perennial turf grass possesses a unique combination of desirable qualities such as slow vertical growth, minimal headings and a bluish deep green color.

For purposes of registration under the "International Convention for the Protection of New Varieties of Plants" (generally known by its French acronym as the UPOV Convention) and noting sections 1612 of the Manual of Patent Examining Procedure, it is proposed that the new variety of Zoysiagrass of the present invention be named "'Himeno' Zoysiagrass."

BRIEF DESCRIPTION OF THE DRAWINGS

FIG. 3 depicts DNA testing of 'Himeno' and other Zoysiagrass varieties using CMN-B42 Primer.

FIG. 4 depicts DNA testing of 'Himeno' and other Zoysiagrass varieties using CMN-B46 Primer.

DETAILED DESCRIPTION OF PREFERRED EMBODIMENTS

Figure 1:
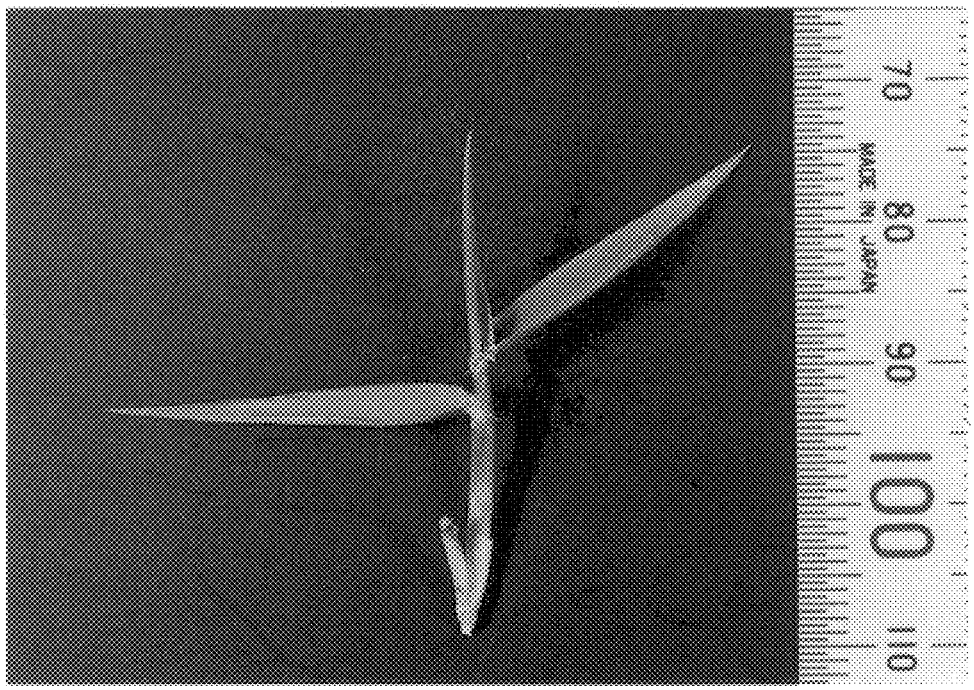
FIG. 1 is a color photograph depicting the leaf blades of 'Himeno', which exhibit a bluish deep green color of 10GY5/6 using the Munsell Color System. The leaf blade is flat, with a round bottom and gradually tapers to an acute point. The first mature leaf is 3.8–4.9 millimeters in width and 3.0–4.5 centimeters long.

'Himeno' was discovered growing in the inventor's Miyachi and Yano Collection in Hiroshima, Japan. Specifically, 'Himeno' was discovered growing in a pot as progeny of one of five strains of *Zoysia japonica* which the inventor had previously collected from Yaku Island, which is located in the southern portion of Kyushu, Japan with a latitude of 30.2 degrees north and a longitude of 130.4 degrees east. As measured from 1980 to 1999, the yearly average temperature of Yaku Island is 19.2° C. and the yearly average rainfall is 4501 mm. The soil type of the land where 'Himeno' was found is a sandy-loam soil.

After collecting the five strains from Yaku Island, the inventor placed each of the five strains of *Zoysia japonica* in individual pots in the "Miyachi and Yano Collection," which is a nursery and research facility specializing in varieties of *Zoysia japonica.* The five pots were numbered and the origin of the Zoysiagrass was noted. Although the five strains of Zoysiagrass retrieved from Yaku Island all are strains of *Zoysia japonica,* none of them have variety names since they were existing in an uncultivated state and have not been commercialized. The five strains brought back from Yaku Island each exhibited a very large plant height and a deep yellowish green color, while 'Himeno' is much shorter and has a bluish deep green color. Two of the five strains brought back from Yaku Island were unable to survive and deteriorated. 'Himeno' emerged from one of these two deteriorated pots. The three surviving strains were designated as 'J-29' (not patented), 'J-30' (not patented) and 'K-1' (not patented).

'Himeno' was discovered growing in sandy-loam soil native to Hiroshima in a pot in the Miyachi and Yano Collection. The location of the Miyachi and Yano Collection has an average mean temperature of 11.5° C. and receives an average of 1.46 meters of rainfall annually. Temperature extremes may approach −10° C. and 33° C. The location of the Miyachi and Yano Collection is 580 meters above sea level.

After discovery, the inventor asexually reproduced 'Himeno' by cutting stolons and rhizomes, rooting them in soil and planting the rooted material to provide planting stock for studying performance and for comparison.

This newly discovered variety of Zoysiagrass is a perennial that exhibits an attractive and striking bluish deep green color, slow vertical growth, minimal headings, low temperature hardiness, low vertical growth, stable growth, and durable stolon. The most distinguishable characteristics of 'Himeno' are its bluish deep green color, slow vertical growth, and minimal headings.

'Himeno' is a durable turf grass well suited to recreation areas and requires less maintenance in comparison to other popular Zoysiagrass varieties such as 'Meyer' (not patented) and 'Emerald' (not patented). The leaf is very short and dense. The stolon is relatively thick and very tough compared to other Zoysiagrass. The grass exhibits very good tolerance to wear and consolidation. It is also quick spreading and has minimal water and fertilizer requirements. The low plant height of 'Himeno' reduces mowing frequency. Thus, 'Himeno' is well adapted to use in sports fields, parks and for water and wind erosion control.

FIG. 3 depicts DNA testing of 'Himeno' and other Zoysia varieties using the RAPD method and CMN-B42 Primer. FIG. 4 depicts DNA testing of 'Himeno' and other Zoysia species using the RAPD method and CMN-B46 Primer. In each testing, template DNA was extracted from the mature leaves of 'Himeno', 'J-29', 'J-30', 'K-1', 'Meyer', 'Victoria' (U.S. Plant Pat. No. 9,135), 'El Toro' (U.S. Plant Pat. No. 5,845), 'Miyako' (U.S. Plant Pat. No. 10,187), 'Emerald', *Zoysia matrella, Zoysia tenuifolia,* and *Zoysia macrostachia* and was replicated with primer using PCR techniques. The amplified products were electorophoresised on agarose gel, stained and photographed. As can be ascertained from the DNA testing, 'Himeno' is distinguishable from the three strains retrieved from Yaku Island (J-29, J-30 and K-1) and the above mentioned Zoysiagrass varieties.

Figure 2:
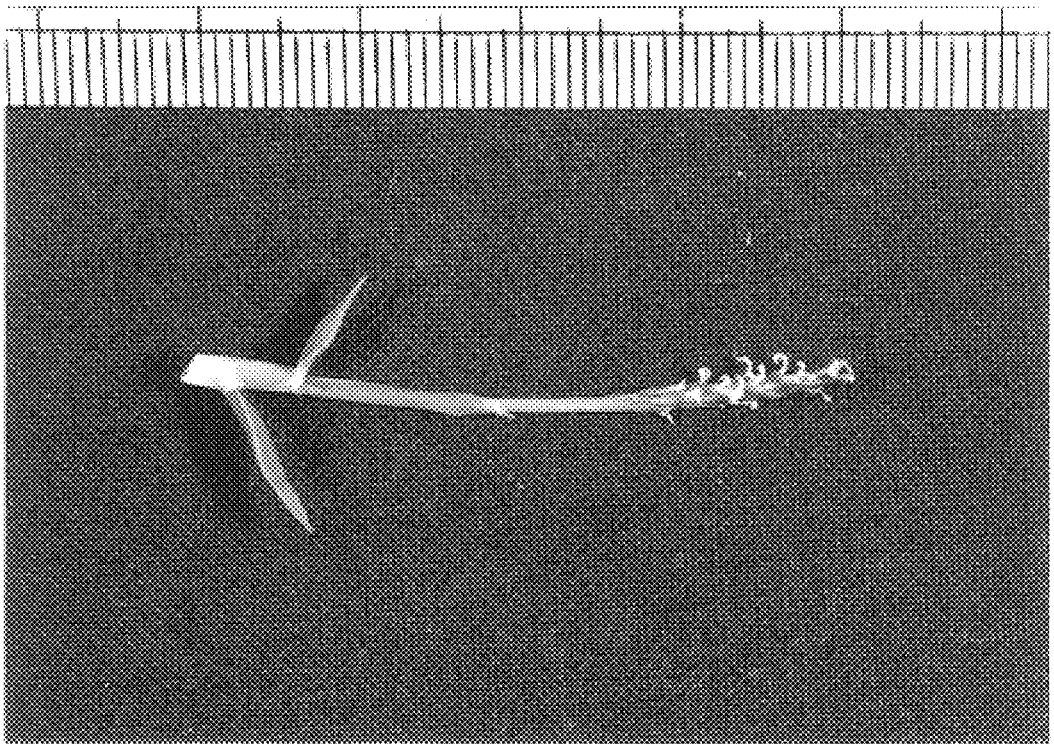
FIG. 2 is a color photograph depicting the spikes of 'Himeno.' The spike contains stigmas of yellowish white color of 1GY9/1 using the Munsell Color System. The glumes are 2.3 millimeters long and are reddish brown color of 7R2.5/6 using the Munsell Color System.

The 'Himeno' plant in FIGS. 1 and 2 is about seven (7) years old. The 'Himeno' plant emerged from a pot containing a deteriorated strain of *Zoysia japonica* collected from Yuka Island in 1992. The photographs of FIGS. 1 and 2 were taken in 1999.

A detailed description of the 'Himeno' Zoysiagrass:

(a) The leaves of 'Himeno' exhibit a bluish deep green color of 10GY5/6 using the Munsell Color System.
(b) The grass grows fast horizontally with an erect very low-growth characteristic.
(c) The grass spreads by stolons and rhizomes, forming the highest dense upright growth among the known varieties of *Zoysia japonica* with a uniform surface and with an extensive root system. The stolons are a very dark red color, 1R2.5/2 using the Munsell Color System. The internodes are 2.0–3.0 centimeters apart and have a diameter of 1.5–2.0 millimeters.
(d) The headings are minimal and the culms are very short. The culms do not rise above plant height.
(e) The leaves are rolled in a bud shoot.
(f) The leave blade is flat, with a round bottom, and gradually tapers to an acute point (see FIG. 1). The leaf veins are prominent and the leaf margins are smooth.
(g) The first mature leaf is 3.8–4.9 millimeters in width and 3.0–4.5 centimeters long.
(h) The leaf blade has a few hairs.
(i) The ligule is a fringe of hairs.
(j) Auricles are absent.
(k) The collar is broad and continuous.
(l) The sheath is glabrous, and split with separate margins.
(m) The entire plant is glabrous, except on the upside of the leaf blade and on the inside of the collar just above the ligule, where several long hairs are present.
(n) The inflorescence consists of a single spike at the top of the main stem (see FIG. 2).
(o) The spikelet contains stigmas of yellowish white color of 1GY9/1 using the Munsell Color System. The glumes are 2.3 millimeters long and are reddish brown color of 7R5/6 using the Munsell Color System.
(p) The seed is sterile and there are very few headings which are hardly found.

The 'Meyer' variety is the closest known variety of Zoysiagrass to 'Himeno.' A description of 'Meyer' is:

(a) 'Meyer' exhibits a deep green leaf color of 7GY5/6 using the Munsell Color System.
(b) 'Meyer' is slightly low growing horizontally, with an erect low growth characteristic.
(c) 'Meyer' spreads by stolons and rhizomes, forming a high dense upright, uniform surface with an extensive root system. The stolons are deep red color of 1R2.5/6 using the Munsell Color System. 'Meyer' has internodes 3.2–4.2 centimeters apart and 1.3–1.8 millimeters in diameter.
(d) The heading is marked.
(e) The leaves are rolled in a bud shoot.
(f) The leaf blade is flat, with a round bottom and gradually tapers to an acute point.
(g) The first mature leaf is 3.8–4.9 millimeters in width and 3.0–4.5 centimeters long.
(h) The leaf blade has a few hairs.
(i) The ligule is a fringe of hairs.
(j) Auricles are absent.
(k) The collar is broad and continuous.
(l) The sheath is glabrous and split with separate margins.
(m) The entire plant is glabrous, except on the upside of the leaf blade and on the inside of the collar just above the ligule, where several long hairs are present.
(n) The inflorescence consists of a single spike at the top of main stem.
(o) The spikelet contains stigmas of pale pink color of 7R9/1 using the Munsell Color System. The glumes are 2.3 millimeters long and are a dark red color of 4R2.5/6 using the Munsell Color System.

What is claimed is:

1. A new and distinct variety of Zoysiagrass plant as described and illustrated herein.

* * * * *

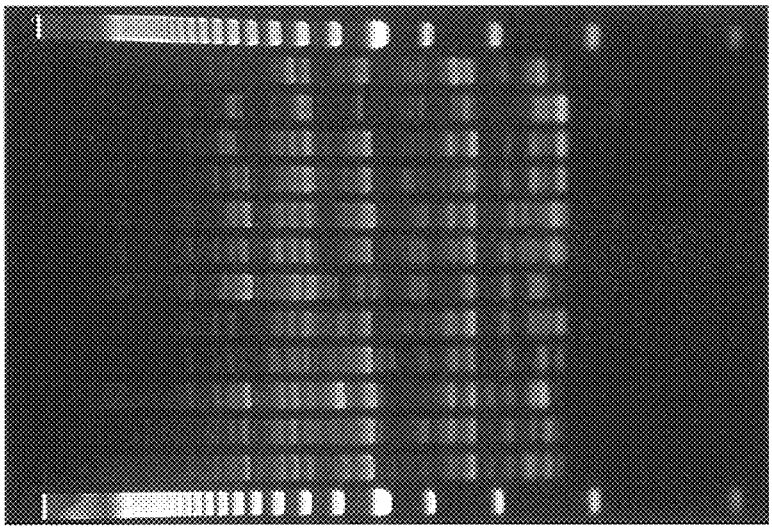
Molecular size marker (250bp)
*Z. macrostachia*
*Z. tenuifolia*
*Z. matrella*
Emerald
Miyako
El Toro
Victoria
Meyer
K-1
J-30
J-29
Himeno
Molecular size marker (250bp)
Figure 3. DNA Finger Print with CMN-B42 Primer ( BEX Co., Ltd. )

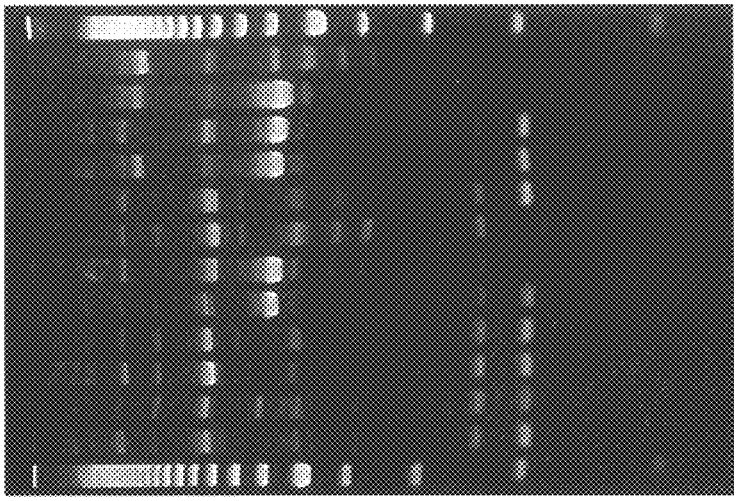
Molecular size marker (250bp)
*Z. macrostachia*
*Z. tenuifolia*
*Z. matrella*
Emerald
Miyako
El Toro
Victoria
Meyer
K-1
J-30
J-29
Himeno
Molecular size marker (250bp)
Figure 4. DNA Finger Print with CMN-B46 Primer ( BEX Co., Ltd )